United States Patent [19]
Arneklev

[11] 3,930,839
[45] Jan. 6, 1976

[54] SUBSTITUTED SULFONATE ANTIDOTE COMPOSITIONS AND METHOD OF USE WITH HERBICIDES

[75] Inventor: Duane R. Arneklev, Sunnyvale, Calif.

[73] Assignee: Stauffer Chemical Company, Westport, Conn.

[22] Filed: Apr. 12, 1974

[21] Appl. No.: 460,663

Related U.S. Application Data

[60] Division of Ser. No. 100,770, Dec. 22, 1970, abandoned, and a continuation-in-part of Ser. No. 68,529, Aug. 31, 1970, abandoned.

[52] U.S. Cl. ............................ 71/100; 71/76; 71/93; 71/103; 71/117; 260/456 R; 260/456 P
[51] Int. Cl.² ................................................ A01N 9/12
[58] Field of Search ............................. 71/93, 100, 77

[56] References Cited
UNITED STATES PATENTS
3,131,509  5/1964  Hoffman .................................... 71/77

*Primary Examiner*—Glennon H. Hollrah
*Attorney, Agent, or Firm*—Daniel C. Block

[57] ABSTRACT

New compounds corresponding to the formula:

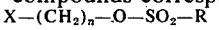

X—(CH₂)ₙ—O—SO₂—R wherein X can be halogen, R can be selected from the group consisting of alkyl, haloalkyl, halogen, acetoxyalkyl, acetoxy haloalkyl, aryl and substituted aryl, and n can be a whole number ranging between 1 and 5. The compositions described herein are used to protect corn from injury by thiolcarbamate herbicides.

1 Claim, No Drawings

SUBSTITUTED SULFONATE ANTIDOTE COMPOSITIONS AND METHOD OF USE WITH HERBICIDES

BACKGROUND OF THE INVENTION

This application is a continuation-in-part of copending application, Ser. No. 68,529, filed Aug. 31, 1970 and a division of Ser. No. 100,770 filed Dec. 22, 1970 both abandoned.

Among the many herbicidal compounds commercially available, the N,N-dialkyl thiolcarbamate herbicides alone or mixed with other herbicides such as triazines have reached a relatively high degree of commercial success. These herbicides are immediately toxic to a large number of weed pests at different concentrations varying with the resistance of the weeds mentioned. Some examples of these compounds are described and claimed in U.S. Pat. Nos. 2,913,327, 3,037,853, 3,175,897, 3,185,720 and 3,198.786. It has been found in practice that the use of the thiolcarbamates as a herbicide in corn fields sometimes causes serious injury to the corn plants. When used in the recommended amounts in the soil to control many broadleaf weeds and grasses, serious malformation and stunting of the corn plants results. This abnormal growth in the corn plants results in loss of crop yield.

DESCRIPTION OF THE INVENTION

It has been discovered that corn plants can be protected against injury by the thiolcarbamates of the above-noted U.S. Patents by adding to the soil an antidote composition having the following formula:

X—(CH$_2$)$_n$—O—SO$_2$—R wherein X can be halogen, R can be selected from the group consisting of alkyl, haloalkyl, halogen, acetoxyalkyl, acetoxy haloalkyl, aryl and substituted aryl, and $n$ can be a whole number from 1 to 5.

The compounds represented by the above formula can be synthesized by mixing together an appropriate alcohol with an appropriate sulfonyl chloride. A solvent such as ethyl ether can be used, if desired. Then, an acid acceptor such as triethylamine is added to the mixture. Essentially quanitative yields of the end product are obtained.

In order to illustrate the merits of the present invention, reference is made to the following examples:

EXAMPLE 1

2-Bromoethyl methanesulfonate

A mixture of 12.5 ml. of 2-bromoethanol, 7.6 ml. of methanesulfonyl chloride and 100 ml. of ether was formed. Then, 14 ml. of triethylamine was added dropwise over a 55 minute period to the formed solution at 5°–10°C. and stirred for 1 hour at 5°–10°C. The mixture was then allowed to stand at room temperature and was stirred for another 15 minutes. To the mixture was added 100 ml. of water, the ether layer separated, dried over magnesium sulfate and evaporated to yield 16 grams of a very light yellow oil. $n_D^{30}$ 1.4801.

EXAMPLE 2

2-Bromoethyl ethanesulfonate

A mixture containing 12.5 ml. of 2-bromoethanol, 12.9 ml. of ethane sulfonyl chloride and 100 ml. of ether was formed. Then, 14 ml. of triethylamine was added dropwise over a 55 minute period at 5°–10°C. and stirred for 1 hour. The mixture was allowed to come to room temperature and stirred for an additional 15 minutes. To the mixture was added 100 ml. of water, the ether layer was separated, dried over magnesium sulfate and evaporated to yield 17.6 grams of a yellow oil. $n_D^{30}$ 1.4760.

EXAMPLE 3

3-Bromopropyl methanesulfonate

A mixture containing 13.9 ml. of 3-bromo-1-propanol, 7.6 ml. of methane sulfonyl chloride and 100 ml. ether was formed. The mixture was mixed together and 14 ml. of triethylamine was added over a period of 45 minutes at 5°–10°C. and then stirred at 5°–10°C. for 1 hour. The mixture was allowed to come to room temperature and was stirred for an additional 15 minutes. To the mixture was added 100 ml. of water and the ether solution dried over magnesium sulfate and evaporated to yield 14.5 g. of a colorless oil. $n_D^{30}$ 1.4749.

EXAMPLE 4

2-Chloroethyl isobutane-sulfonate

A mixture was formed containing 6.7 ml. of ethylene chlorohydrin, 70 ml. of ether and 15.6 g. of isobutane sulfonyl chloride. Then, 14 ml. of triethylamine was added dropwise to the mixture with stirring in an ice bath over a period of 30 minutes at 12°–14°C. While stirring the mixture was allowed to warm to 23°C. (1 hour) and was then washed with water (100 ml.), dried over magnesium sulfate and evaporated to yield 19.7 g. of a colorless oil. $n_D^{30}$ 1.4502.

Other compounds were prepared in an analogous manner starting with the appropriate starting materials as outlined above. The following is a table of compounds representative of those embodied by the present invention. Compound numbers have been assigned to them and are used for identification throughout the balance of the specification.

TABLE I

| Compound Number | \multicolumn{3}{c}{X—(CH$_2$)$_n$—O—SO$_2$—R} | | |
|---|---|---|---|
| | n | X | R |
| 1 | 2 | Br | CH$_3$ |
| 2 | 2 | Br | C$_2$H$_5$ |
| 3 | 3 | Br | CH$_3$ |
| 4 | 2 | Cl | CH$_2$—CH(CH$_3$)$_2$ |
| 5 | 3 | Br | CH$_2$—CH(CH$_3$)$_2$ |
| 6 | 2 | Br | CH$_2$—CH(CH$_3$) |
| 7 | 2 | Br | 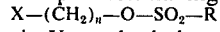—CH$_3$ |
| 8 | 2 | Br | (CH$_2$)$_3$CH$_3$ |
| 9 | 2 | Cl | CH$_3$ |
| 10 | 2 | Br | CH$_2$—C(=O)—O—CH$_2$—CH$_2$—Br |
| 11 | 2 | Br | CH$_2$Cl |
| 12 | 2 | Br | (CH$_2$)$_5$CH$_3$ |
| 13 | 3 | Br | CH$_2$Cl |
| 14 | 3 | Br | (CH$_2$)$_5$CH$_3$ |

TABLE I-continued $X-(CH_2)_n-O-SO_2-R$

| Compound Number | n | X | R |
|---|---|---|---|
| 15 | 2 | Cl | OCH$_2$CH$_2$Cl |
| 16 | 2 | Br | Cl |
| 17 | 4 | Br | CH$_3$ |
| 18 | 2 | Br | CH$_2$—C$_6$H$_5$ |
| 19 | 2 | I | CH$_3$ |
| 20 | 2 | Br | CH$_2$CH$_2$CH$_2$Cl |

The compositions of this invention were tested in the following manner.

Test 1: Soil Incorporation

Metal flats measuring 8 × 12 × 3 inches in area were filled with 10 lbs. of Felton loamy sand soil. The herbicide and herbicide antidote were applied separately or in combination to the soil as it is mixed in a five-gallon cement mixer. The following stock solutions were made up of each compound when the herbicide and antidote were applied separately. In making the stock solutions of the herbicide, 936 mg. of 75.5% active ingredient was diluted with 100 ml. of water. For the antidote, 700 mg. of technical material was diluted with 100 ml. of acetone. One ml. of these stock solutions is equivalent to 7 mg. active ingredient or one pound per acre when this treated soil was placed into 8 × 12 × 3 inch flats. After the soil was treated with the herbicide and the antidote at the desired rates, the soil was transferred from the cement mixer back into 8 × 12 × 3 inch flats where it was now ready for planting corn seed. A pint sample of soil was then removed from each flat and retained for covering the seeds after planting. The soil was leveled and rows one-half inch deep were made in each flat. Enough DeKalb XL 374 corn seeds were planted to obtain good stands in each treatment. Seeds were then covered up with the one pint of soil which had been removed just prior to planting.

The flats were then placed on greenhouse benches where temperatures were between 70°–90°F. The flats were watered by sprinkling as needed to assure good plant growth until rated. The crop tolerance was rated after two or three weeks. The results of these tests are set forth in Table II.

Test 2: Corn Seed Treatment

Metal flats measuring 8 × 12 × 3 inches in area were filled with 10 lbs. of Felton loamy sand soil. Soil incorporated herbicides were applied at this time. The soil from each flat was placed into a five-gallon cement mixer where the soil was mixed as the herbicides were applied as a stock solution by adding 936 mg. of 75.5% active ingredient to 100 ml. of water. One ml. of stock solution was applied to the soil in a volumetric pipet for each pound of herbicide desired. One ml. of stock solution contains seven mg. of herbicide which equals one pound per acre when applied to soil in 8 × 12 × 3 inch flats. After the herbicide incorporation, the soil was placed back into the flats.

Flats of herbicide-treated and untreated soil were then ready to be planted. A pint sample of soil was then removed from each flat and placed next to each flat for later use in covering up the seeds. The soil was leveled and rows one-half inches deep were made for planting seeds. Alternating rows of treated and untreated crop seeds were sown. In each test six DeKalb XL 374 field corn seeds were planted in each row. Rows were approximately 1 ½ inches apart in the flat. Seed treatment was applied by placing 50 mg. of the seed treatment compound with 10 grams of corn seed in a suitable container and shaking them until the seeds were uniformly covered with the seed treatment. Seed treatment compounds were applied as liquid slurries and powder or dust treatments. In some cases acetone was used to dissolve powdered or solid compounds so they could be more effectively applied to the seeds.

After flats were seeded they were covered with the one pint of soil which had been removed just prior to planting. Flats were placed on greenhouse benches where temperatures ranged from 70°–90°C. Flats were watered by sprinkling as needed to assure good plant growth. Percent control ratings were taken two to three weeks after treatments were applied.

In each test, the herbicide is applied alone, in combination with the seed protectant and the seed protectant is applied alone to check for phytotoxicity. The results of these tests are tabulated in Table III. It should be noted that Run Nos. 7 thru 10 were carried out in styrofoam flats measuring 5 × 7 × 2 ¾ inches with all other conditions remaining the same.

TABLE II

| Herbicide | Rate lb/A | Compound No. 1 lb/A | Compound No. 2 lb/A | Compound No. 3 lb/A | Injury to Corn % |
|---|---|---|---|---|---|
| EPTC* | 6 | 1 | | | 30 ST MF |
| EPTC* | 6 | 10 | | | 10 ST |
| EPTC* | 6 | 100 | | | 90 ST |
| EPTC* | 6 | | 1 | | 50 ST MF |
| EPTC* | 6 | | 10 | | 20 ST |
| EPTC* | 6 | | | 1 | 40 ST MF |
| EPTC* | 6 | | | 10 | 10 ST |
| EPTC* | 6 | | | | 98 MF |
| | | 1 | | | 10 ST |
| | | 10 | | | 20 ST |
| | | 100 | | | 90 ST |
| | | | 1 | | 0 |
| | | | 10 | | 20 ST |
| | | | | 1 | 0 |
| | | | | 10 | 10 ST |
| EPTC* | 3 | 1 | | | 0 |
| EPTC* | 3 | 10 | | | 20 ST |
| EPTC* | | | | | 98 MF |
| EPTC* + 2-Chloro-4-ethylamino-6-isopropylamino-s-triazine | 6+ 1 | 1 | | | 10 MF |
| EPTC* + | 6+ | | | | |

TABLE II-continued

| Herbicide | Rate lb/A | Compound No. 1 lb/A | Compound No. 2 lb/A | Compound No. 3 lb/A | Injury to Corn % |
|---|---|---|---|---|---|
| 2-Chloro-4-cyclopropylamino-6-isopropylamino-1,3,5-triazine | 1 | 1 | | | 0 |
| EPTC + 2,4-dichlorophenoxy-acetic acid | 3+1½ | 1 | | | 20 ST |
| EPTC + 2,4-dichlorophenoxy-acetic acid | 3+1½ | 0 | | | 75 ST MF |
| S-propyl dipropylthiocarbamate | 6 | 1 | | | 10 MF |
| S-propyl dipropylthiocarbamate | 6 | 0 | | | 98 MF |
| S-ethyl cyclohexylethyl-thiocarbamate | 6 | 1 | | | 25 MF |
| S-ethyl cyclohexylethyl-thiocarbamate | 6 | 0 | | | 90 MF |
| S-ethyl diisobutylthiocarbamate | 12 | 2 | | | 0 |
| S-ethyl diisobutylthiocarbamate | 12 | 1 | | | 0 |
| S-ethyl diisobutylthiocarbamate | 12 | 0 | | | 75 MF |

ST = Stunt; MF = Malformation
*EPTC = S-ethyl-N,N-dipropylthiolcarbamate

TABLE III

| Run No. | Compound No. | EPTC lb/A | Seed Treatment % W/W | Percent Injury to Corn Treated Seed | Percent Injury to Corn Untreated Seed in Adjacent Row |
|---|---|---|---|---|---|
| 1 | 1 | 6 | 0.5 | 90 ST | 20 ST MF |
| 2 | 2 | 6 | 0.5 | 50 ST | 20 ST MF |
| 3 | 3 | 6 | 0.5 | 25 ST | 30 ST MF |
| 4 | 1 | — | 0.5 | 90 ST | 0 |
| 5 | 2 | — | 0.5 | 50 ST | 0 |
| 6 | 3 | — | 0.5 | 20 ST | 0 |
| 7 | 1 | 6 | 0.005 | 75 MF | 94 MF |
| 8 | 1 | 6 | 0.05 | 13 ST | 15 ST MF |
| 9 | 1 | — | 0.005 | 0 | 0 |
| 10 | 1 | — | 0.05 | 23 ST | 0 |

ST = Stunt;
MF = Malformation

The antidote compounds of the present invention can be used in any convenient form. Thus, the antidote compounds can be made into emulsifiable liquids, emulsifiable concentrates, liquid, wettable powder, powders, granular or any other convenient form. In its preferred form, the antidote compounds are admixed with the N,N-dialkyl thiolcarbamates and incorporated into the soil prior to or after planting the corn seed. It is to be understood, however, that the thiolcarbamate herbicide can be incorporated into the soil and thereafter the antidote compound can be incorporated into the soil. Moreover, the corn seed can be treated with the antidote compound and planted into the soil which has been treated with herbicides or untreated with the herbicide and subsequently treated with the herbicide. The addition of the antidote compound does not affect the herbicidal activity of the carbamate compounds.

The amount of antidote composition present can range between about 0.01 to about 15 parts by wt. per each part by wt. of thiolcarbamate herbicide. The exact amount of antidote compound will usually be determined on economic ratios for the most effective amount usable.

What is claimed is:

1. In the method of controlling weeds wherein an effective amount of a thiolcarbamate herbicide is added to the habitat thereof the improvement comprising adding to the habitat thereof from about 0.01 to about 15 parts by weight for each part by weight of the herbicide an antidote compound represented by the formula:

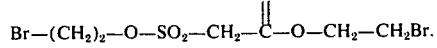

* * * * *